United States Patent
Urry et al.

[11] 3,957,825
[45] May 18, 1976

[54] PROCESS FOR SYNTHESIZING ZEARALANONE AND RELATED COMPOUNDS

[75] Inventors: Wilbert Herbert Urry, Chicago, Ill.; Guy Towns Mullenbach, Berkeley, Calif.

[73] Assignee: Commercial Solvents Corporation, Terre Haute, Ind.

[22] Filed: Nov. 27, 1974

[21] Appl. No.: 527,843

Related U.S. Application Data

[62] Division of Ser. No. 247,414, April 25, 1972, Pat. No. 3,862,982.

[52] U.S. Cl. ........................................ 260/343.2 F
[51] Int. Cl.$^2$ ...................................... C07D 313/00
[58] Field of Search ............................ 260/343.2 F

[56] References Cited
UNITED STATES PATENTS

| | | | |
|---|---|---|---|
| 3,631,179 | 12/1971 | Urry .............................. | 260/343.2 F |
| 3,810,918 | 5/1974 | Urry et al. ...................... | 260/343.2 F |
| 3,836,544 | 9/1974 | Urry et al. ...................... | 260/343.2 F |

*Primary Examiner*—James A. Patten
*Attorney, Agent, or Firm*—Morton, Bernard, Brown, Roberts & Sutherland

[57] ABSTRACT

This invention provides a new synthesis for zearalanone and for related compounds having more or fewer carbon atoms in the non-aromatic ring than does zearalanone, which related compounds and zearalanone are represented by the formula

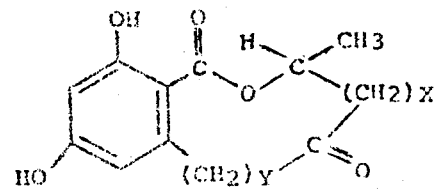

wherein X is an integer having a value from 2 to 6 inclusive and Y is an integer having a value from 2 to 8 inclusive. It also provides for new methods of making compounds useful in the synthesis of zearalanone and related compounds.

The new compounds useful as intermediates are 2,7-octadienoic acid; methyl 2,7-octadienoate; sodium ethyl 6-(4-pentenyl)-β-dihydroresorcylate; ethyl 6-(4-pentenyl)-β-dihydroresorcylate; sodium methyl 6-(4-pentenyl)-β-dihydroresorcylate; methyl 6-(4-pentenyl)-β-dihydroresorcylate; methyl 3-bromo-6-(4-pentenyl)-β-dihydroresorcylate; methyl 6-(4-pentenyl)-β-resorcylate; ethyl 6-(4-pentenyl)-β-resorcylate; ethyl 6-(4-pentenyl)-β-resorcylate dibenzyl ether; and 4-penten-2-yl 6-(4-pentenyl)-β-resorcylate dibenzyl ether.

3 Claims, No Drawings

PROCESS FOR SYNTHESIZING ZEARALANONE AND RELATED COMPOUNDS

This is a division of application Ser. No. 247,414, filed Apr. 25, 1972 now matured to U.S. Pat. No. 3,862,982 issued Jan. 28, 1975.

BRIEF SUMMARY OF THE INVENTION

The present application describes a new process for the manufacture of zearalanone and related compounds, which related compounds and zearalanone are represented by the formula

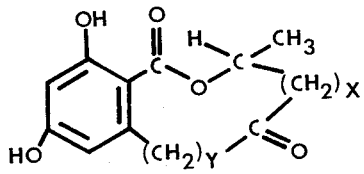

wherein X is an integer having a value from 2 to 6 inclusive and Y is an integer having a value from 2 to 8 inclusive. More specifically the invention relates to a process for making all of the foregoing compounds by a new series of process steps utilizing new intermediate compounds.

It is an object of the present invention to provide a new means for synthesizing zearalanone and related compounds.

It is another object of the invention to provide new intermediates useful in the preparation of zearalaone and related compounds.

It is a further object of the invention to provide new processes for producing intermeidate compounds useful in the synthesis of zearalanone and related compounds.

DETAILED DESCRIPTION

Zearalanone, whose synthesis is one of the objects of this invention, has the structure illustrated by the formula:

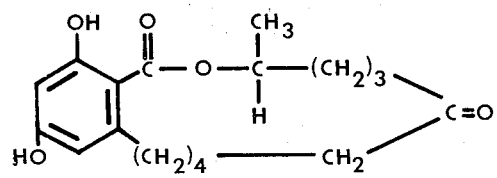

An examination of the above formula reveals that it has one asymmetric carbon atom. Hence, this synthesis gives a mixture of two enantiomorphs designated as D and L by the older Fischer convention and by R and S by the newer convention of Cahn and Ingold (Cahn, R. S. and Ingold, C. K., J. Chem. Soc. 612, (1951Cahn, R. S. J. Chem. Educ. 41, 116 (1964).

Zearalanone produced by the reduction of natural zearalenone has the same S configuration as does the parent compound. The chemical name for zearalanone is: 6-(10-hydroxy-6-keto-undecyl)-β-resorcylic acid lactone. Zearalanone was one of the compounds described and claimed in U.S. Pat. No. 3,239,341 issued Mar. 8, 1966 to Hodge et al. The compound was prepared by the reduction of a natural product zearalenone, sometimes referred to as F.E.S. resulting from the fermentation of suitable nutrient media using the organism Gibberella zeae (Gordon) on deposit at the Northern Utilization Research and Development Division of the U.S. Department of Agriculture at Peria, Ill under the number NRRL-2830. The reduction was carried out by hydrogen under the influence of a catalyst such as palladium or platinum on char in a menstruum of ethyl alcohol (Tetrahedron Letters No. 27, pages 3109–3114, 1966).

The present invention is concerned with the discovery that zearalanone can be made readily by the sequence of reactions illustrated in Chart I.

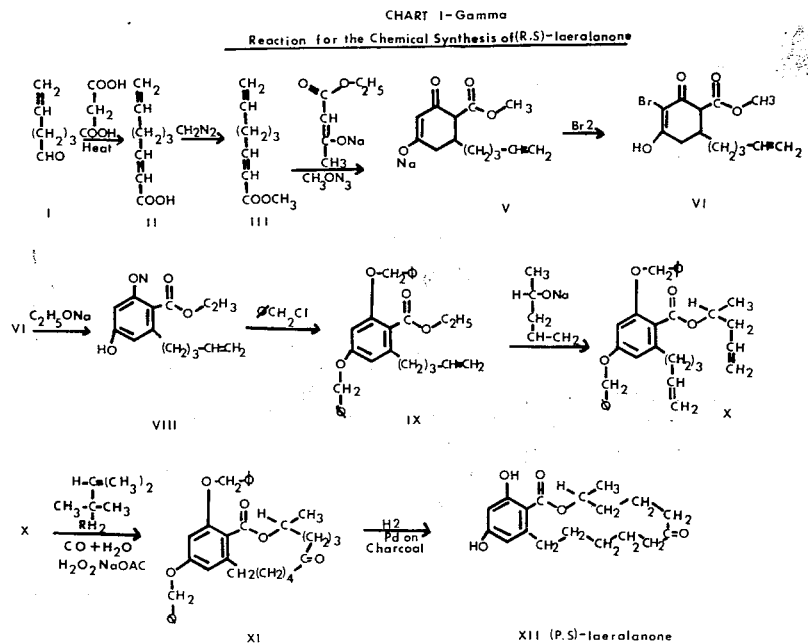

The first step in the sequence in the pyrolysis of 3-hydroxy-1,5-hexadiene to prepare 5-hexenal which is reacted with malonic acid to form 2,7-octadienoic acid. The foregoing acid is esterified by treatment with diazomethane and the resulting methyl ester is reacted with the sodium salt of ethyl acetoacetate under the influence of sodium methoxide in a methanol menstruum to yield the sodium salt of methyl 6-(4-pentenyl)-β-dihydroresorcylate. The dihydroresorcylate sodium salt is then brominated at low temperature to form methyl 3-bromo-6-(4-pentenyl)-β-dihydroresorcylate which is de-hydrobrominated by treatment with sodium ethoxide in an anhydrous ethanol menstruum to prepare ethyl 6-(4-pentenyl)-β-resorcylate. The foregoing resorcylate is reacted with benzyl chloride to yield ethyl 6-(4-pentenyl)-β-resorcylate dibenzyl ether which is treated with the sodium alcoholate of 4-penten-2-ol to produce 4-penten-2-yl 6-(4-pentenyl)-β-resorcylate dibenzyl ether. The foregoing compound is treated successively with 2,3-dimethyl-2-butylborane, carbon monoxide, sodium acetate solution, and hydrogen peroxide to form zearalanone dibenzyl ether. On Hydrogenation zearalanone dibenzyl ether is converted to (R,S)-zearalanone.

The foregoing sequence of reactions, as well as the reactions described in the specific example, can be carried out with appropriate starting materials to yield compounds related to (R,S)-zearalanone. They can be represented by the following formula:

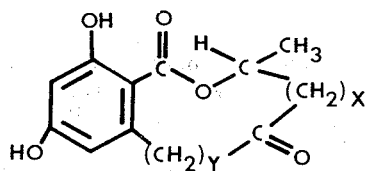

Where X and Y are integers which can take the values:

X = 2, 3, 4, 5, or 6.

Y = 2, 3, 4, 5, 6, 7, or 8.

The values of X and Y for zearalanone are underscored.

For example, in order to prepare the compound where X = 2 and Y = 2, it is necessary to start with acrolein ($CH_2$=CH-CHO) as Compound I of Chart I and to use the sodium alcoholate of 3-buten-2-ol in the reaction with the Compound IX (ethyl 6-(4-ethenyl)-β-resorcylate dibenzyl ether).

The compounds produced by the process of this invention are useful in promoting the growth rate of meat producing animals. The compounds can be administered to animals by any suitable method including subcutaneous injection of pellets under the skin of the ears of mammals as well as by oral and parenteral administrations. For example, the compounds can be formulated into pellets and put under the skin of the ear by a suitable gun or they can be suspended in a medium such as peanut oil and injected parenterally. The compounds can also be blended with ordinary feed containing nutritional values in an amount sufficient to produce the desired rate of growth and can thus be fed directly to animals.

When the compounds are to be fed directly to animals, the feed composition can be prepared containing the usual nutritionally balanced quantities of fats, carbohydrates, proteins, vitamins, and minerals together with the chosen compound. Some of these usual dietary elements are grains, such as ground grain and grain by-products; animal protein substances such as those found in fish meal and meat scraps; animal and vegetable fats; vegetable proteins like soybean oil meal or peanut oil meal; vitaminaceous materials, e.g. vitamin A and D mixtures; riboflavin supplements and other vitamin B complex members; antibiotic supplements such as zinc bacitracin feed grade; and bone meal and limestone to provide minerals. A type of conventional feed material for use with cattle includes alfalfa hay and ground corn cobs together with supplementary antibiotics and vitaminaceous materials if desired.

The amount of compound administered to the animal, of course, depends upon the specific animal, its age and sex, and the desired rate of growth. Usually, administration of from about 1 to about 100 mg of a compound per animal per day produces significantly increased growth rate.

The following examples serve to illustrate the invention and set forth the best mode contemplated by the inventors for carrying out the invention.

The abbreviations used in the following examples aare described in these paragraphs. The description of a nuclear magnetic resonance (nmr) scan is identified by the letters nmr followed by the solvent and reference substance placed in parenthesis; thus, nmr (C $Cl_3$, TMS) means that the scan was made with deuterated chloroform as the solvent and tetramethylsilane as the reference substance. The position of the identified peaks may be described by the value:

$\delta$ = cycles per second from TMS divided by sixty (This relation applies with a 60 megaherz instrument)

$\delta$ = c.p.s. ÷ 60 or by $\pi$ = ten minus $\delta$ (10—$\delta$)

The type of peak is shown by the first letter of the word describing the peak and is followed by a numeral indicating the number of hydrogen atoms involved. Examples are as follows:

| | | |
|---|---|---|
| s,1 | = | singlet, one hydrogen |
| s,2 | = | singlet, two hydrogens |
| d,1 | = | doublet, one hydrogen |
| t,2 | = | triplet, two hydrogens |
| m,4 | = | multiplet, four hydrogens |
| broad s,1 | = | a broad singlet for one hydrogen, which may result from O$\underline{H}$, COO$\underline{H}$, C$\underline{H}$O. |

Coupling constants are valuable for identification of the positions of hydrogen atoms and with respect to variations of the electronic environments. The coupling constants are measured as the distance between the peaks in question on the x-axis of the scan and are recorded as J values in terms of c.p.s.

Cycles per second are denoted by c.p.s. and by Hz.

In all of the examples, the temperatures are in degrees centigrade. In the nmr data, TMS is tetramethylsilane; DSS is sodium 2,2-dimethyl-2-silapentane-5-sulfonate.

In the following specific examples, the specific compounds used are such that in the general formulae presented herein X = 3 and Y = 5. The specific reactions, however, are illustrative of the more general reactions when the compounds are generally represented with X being an integer of 2 to 6 (i.e. 2, 3, 4, 5 or 6) and Y being an integer of 2 to 8 (i.e. 2, 3, 4, 5, 6, 7 or 8). In the following described general reactions the letter W and Z are also used to represent integers with W being an integer of from 0 to 6 (i.e. 0, 1, 2, 3, 4, 5 or 6) and Z being an integer from 0 to 4 (i.e. 0, 1, 2, 3 or 4). It should also be noted that a relationship exists between X and Z, such that when zearalanone or a related compound is described with the X in the general formula e.g. X = 3, the Z compound should be selected such that Z = X − 2 or in this illustration with X = 3, Z would equal 1. Similarly, a relationship exists between W and Y, such that when a zearalanone or a related compound is described with the Y in the general formula e.g. Y = 5, the W compound should be selected such that W = Y − 2 or in this illustration with Y = 5, W would equal 3.

EXAMPLE 1

This example illustrates the preparation of 5-hexenal I by the following reaction:

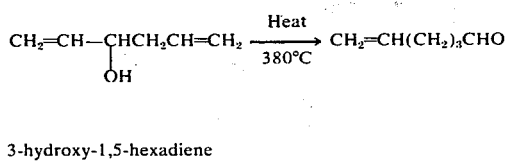

3-hydroxy-1,5-hexadiene         I 190 g, 1.94 mol, of 3-hydroxy-1,5-hexadiene was slowly distilled through a 50 cm column packed with 3 mm Pyrex helices maintained at 380°. Fractional distillation of the pyrolysis mixture gave 111.2 g, 1.14 mol (59 percent), of 5-hexenal: bp 57.5° (57 mm); bp 120°–21°(760 mm).

Although 5-hexenal is not a new compound, it is not readily available and, therefore, the above described step is a known method for the preparation of it.

EXAMPLE 2

This example illustrates the preparation of 2,7-octadienoic acid II by the following general reaction wherein W = 3:

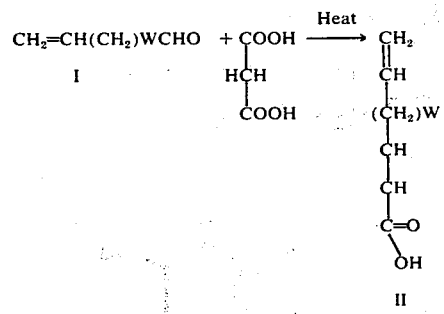

A reaction mixture containing 76.9 g, 0.784 mol, of 5-hexenal I, 90.0 g 0.865 mol, of malonic acid, and 145 ml of pyridine was stirred at 25° under nitrogen for 60 hr. An additional 45.0 g of malonic acid was added to it, and stirring was continued for 24 hr at 25°. It was then heated on a steam bath until carbon dioxide evolution ceased (20 hr). Water (145ml) was added to it, and the resulting mixture was extracted with ether (3 × 200 ml). The extract was washed with dilute hydrochloric acid (2N, 2 × 50 ml), water (2 × 50 ml), and dried ($Na_2SO_4$). Fractional distillation gave 83.0 g, 0.593 mol (76 percent), of II: bp 86°–87° (0.15 mm); nmr ($CDCL_3$, TMS) $\delta$12.34 (s, 1, COO$\underline{H}$), 7.26 and 6.98 (2 t, 1, $J_{AB}$ = 15.7 Hz, $J_{AX}$ = 7 Hz, $CH_2C\underline{H}=CH$), 5.97 and 5.70 (2 t, 1, $J_{AB}$ = 15.7 Hz, $J_{BX}$ = 1 Hz, $CHCOO$), 5.72, 4.92 and 4.88 (3 m, 3,$C\underline{H}=C\underline{H}$), 2.12 (br m, 4, $C\underline{H}_2CH=CH_2$), and 1.60 ppm (br m, 2, $CH_2C\underline{H}_2CH_2$). Anal. Calcd. for $C_8H_{12}O_2$: C, 68.6; H, 8.6. Found: C, 68.6; H, 8.7.

EXAMPLE 3

This example illustrates the preparation of methyl 2,7-octadienoate III by the following general reaction wherein W= 3:

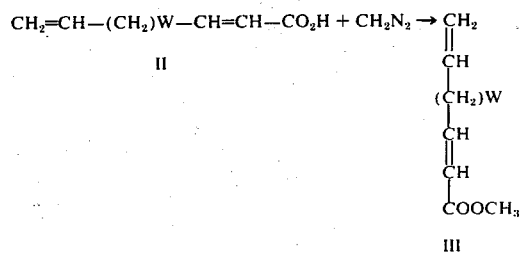

A solution of diazomethane in ether was added to a cold (0°) solution of 83.0 g, 0.592 mol, of II in 200 ml of ether until a yellow color persisted. Evaporation of the reaction mixture gave 90.3 g of crude III that was fractionally distiled to give 80.2 g, 0.520 mol (88 percent) of III: bp 44°–45° (0.70 mm); nmr ($CDCl_3$, TMS) $\delta$7.04 and 6.78 (2 t, 1, $J_{AB}$ = 15.7 Hz, $J_{AX}$ = 7 Hz, $CH_2C\underline{H}=CH$), 5.87 and 5.61 (2 t, 1, $J_{AB}$ = 15.7 Hz, $J_{BX}$ = 1 Hz, CHCO), 5.72, 4.92 and 4.88 (3 m, 3, $C\underline{H}=C\underline{H}_2$), 3.67 (s, 3, $C\underline{H}_3$), 2.12 (br m, 4, $C\underline{H}_2CH=CH_2$), and 1.58 ppm (br m, 2, $CH_2CH_2CH_2$). Anal. Calcd. for $C_9H_{14}O_2$: C, 70.2; H, 9.1. Found: C, 70.1; H, 9.2.

EXAMPLE 4

This example illustrates the preparation of sodium ethyl 6-(4-pentenyl)-$\beta$-dihydroresorcylate IV by the following general reaction wherein W = 3:

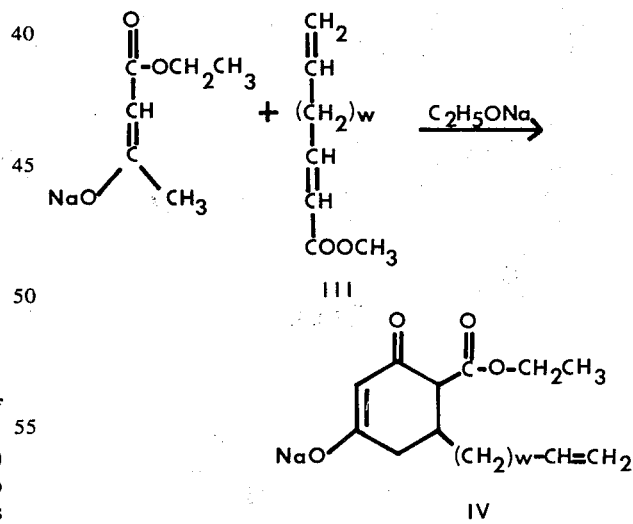

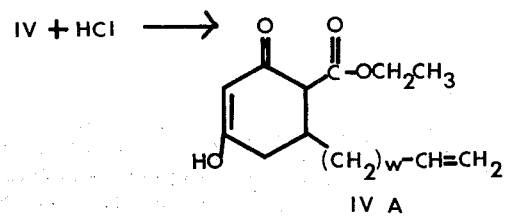

81.4 g, 0.626 mol, of freshly-distilled ethyl acetoacetate was added dropwise to a stirred solution of sodium ethoxide prepared from 14.4 g, 0.626 g-atom of sodium and 200 ml of ethanol under nitrogen. The resulting solution was held at reflux while 80.2 g, 0.521 mol, of III was added dropwise, and then such heating was continued with mechanical stirring for 22 hr. The solid that precipitated during the reaction and while te mixture was cooled to 0° was removed on a filter, and it was washed with ether to give 110.80 g, 0.404 mol (78 percent), of white IV: nmr ($D_2O$, DSS, integration of some ring hydrogen atoms not given since they exchanged) δ5.72, 4.92 and 4.88 (3 m, 3 C$\underline{H}_2$=CH), 4.22 (q, 2, J = 7 Hz, COOC$\underline{H}_2$), 3.18 (d, J = 10 Hz, HCCOO), 2.20 (m, OCC$\underline{H}_2$CH), 2.00 (br m, 2, C$\underline{H}_2$C$\underline{H}_2$), 1.33 (br m, 5, C$\underline{H}$(C$\underline{H}_2$)$_2$-C$\underline{H}_2$), and 1.26 ppm (t, 3, J = 7 Hz, C$\underline{H}_3$).

Then a solution of 3.00 g, 0.0109 mol, of IV in 50 ml of water was acidified with 3N hydrochloric acid and the resulting mixture was extracted with ether (4 × 25 ml). The extract was washed with water (4 × 25 ml), dried (MgSO$_4$), and evaporated in a Rinco brand of vacuum rotary evaporator, a well known and widely used vacuum rotary evaporator hereinafter referred to as "Rinco", to give a residue which crystallized from ligroin (bp 60°–68°) to give 2.37 g, 0.00942 mol (86 percent), of ethyl 6-(4-pentenyl)-β-dihydroresorcylate IV A: mp 72.5°–73.5°; nmr (CDCl$_3$, TMS) δ12.32 (s, 0.2, 2-O$\underline{H}$), 9.75 (s, 0.8, 4-O$\underline{H}$), 5.72, 4.92 and 4.88 (3 m, 3, C$\underline{H}$=C$\underline{H}_2$), 5.52 (s, 0.8, 3-C$\underline{H}$), 4.29 and 4.22 (2 q, 2, J = 7 Hz, COOC$\underline{H}_2$), 3.12 (s, 0.4, 3-C$\underline{H}_2$), 3.15 (d, 0.8, J = 10 Hz, 1-C$\underline{H}$), 2.45 (m, ca. 2, 5-C$\underline{H}_2$), 2.06 (br m, 2, C$\underline{H}_2$CH=CH$_2$), 1.36 (br m, 5, C$\underline{H}$(C$\underline{H}_2$)$_2$CH$_2$), and 1.29 ppm (t, 3, J = 7 Hz, C$\underline{H}_3$). Anal. Calcd. for $C_{14}H_{20}O_4$: C, 66.7; H, 8.0. Found: C, 66.7; H, 8.0.

EXAMPLE 5

This example illustrates the preparation of methyl 6-(4-pentenyl)-β-dihydroresorcylate sodium salt V by the following general reaction wherein W = 3:

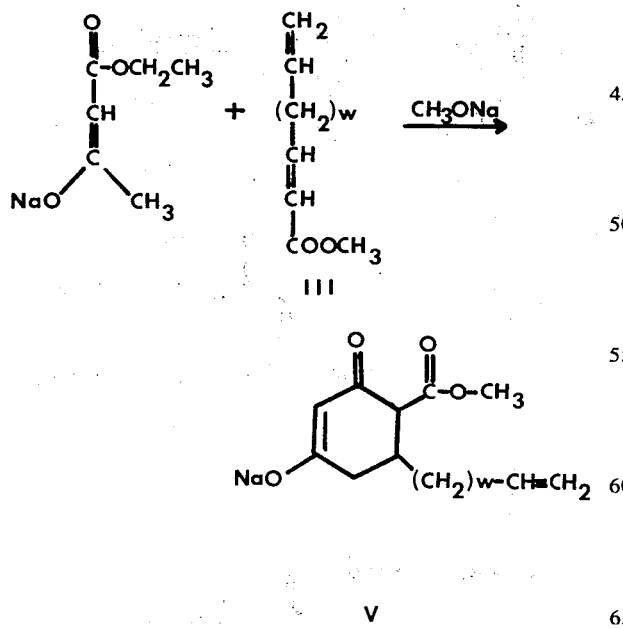

The reaction mixture was prepared by dropwise addition of 70.7 g, 0.598 mol, of ethyl acetoacetate to a solution of 32.3 g, 0.598 mol of sodium methoxide in 130 ml of methanol stirred under nitrogen, and then 74.2 g, 0.482 mol of III was also added dropwise. It was held at reflux with mechanical stirring for 20 hr. About 60 ml of its solvent was removed under vacuum, and it was cooled to 0°. A precipitate that formed during the above was removed on a filter and washed with ether until it was white to give 84.7 g, 0.326 mol (68 percent), of V: nmr (D$_2$O, DSS, again exchange of hydrogen atoms on the ring occurred) δ5.72, 4.92 and 4.88 (3 m, 3, C$\underline{H}$=C$\underline{H}_2$), 5.07 (s, OCC$\underline{H}$CO), 3.18 (d, J = 10 Hz, $\underline{H}$CCOO), 2.20 (m, OCC$\underline{H}_2$CH), 2.00 (br m, 2, C$\underline{H}_2$CH=CH$_2$), and 1.33 ppm (br m, 5, C$\underline{H}$(C$\underline{H}_2$)$_2$C$\underline{H}_2$). The nmr spectrum is nearly the same as IV above, except for the alkoxy absorptions.

The compound V may readily be acidified to prepare methyl 6-(4-pentenyl)-β-dihydroresorcylate VA by the following general reaction wherein W = 3:

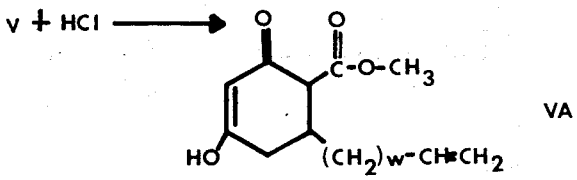

Methyl 6-(4-pentenyl)-β-dihydroresorcylate when w = 3

And in turn the compound VA may be reacted with sodium hydroxide to form V. Converting the sodium salt V to VA and then treating VA with sodium hydroxide to again form the sodium salt V, of course, provides an efficient method for preparing relatively pure V.

EXAMPLE 6

This example illustrates the preparation of methyl 3-bromo-6-(4-pentenyl)-β-dihydroresorcylate VI by the following general reaction wherein W = 3:

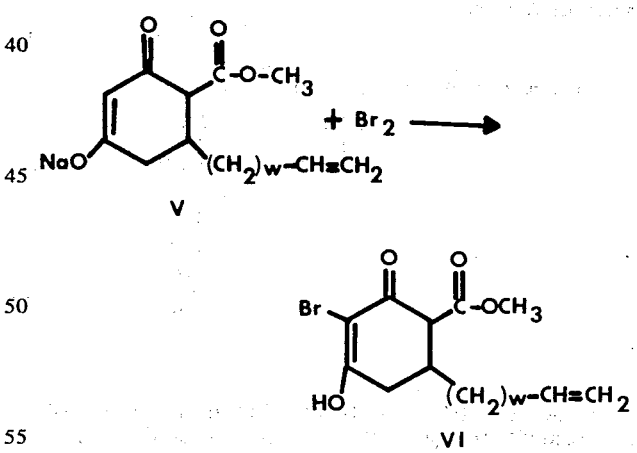

A solution of 58.2 g, 0.326 mol, of bromine and 193.1 g, 1.87 mol, of sodium bromide in 200 ml of water was added dropwise over 6 hr to a rapidly stirred solution of 84.7 g, 0.326 mol, of V in 700 ml of water cooled to 0°. After 30 min, the solid that had precipitated was removed by filtration. It was dissolved in 200 ml of ether, and the resulting solution was washed with water (3 × 150 ml), and briefly dried (MgSO$_4$). It was evaporated (Rinco, 25°), and the residue was recrystallized from 200 ml of ether and pentane to give 70.4 g, 0.222 mol (68 percent), of white crystalline VI: mp 91°–93°; nmr (CDCl$_3$, TMS) δ8.10 (s, 1, 4-O$\underline{H}$), 5.72, 4.92 and 4.88 (3 m, 3, C$\underline{H}$=C$\underline{H}_2$), 3.77 (s, 3, C$\underline{H}_3$), 3.25 (d, 1, J = 10 Hz, $\underline{H}$CCOO), 2.72 (dd, 1 J$_{AB}$ = 20.4 Hz, J$_{AX}$ = 11.0 Hz, OCC$\underline{H}_2$CH), 2.43 (dd, 1, J$_{AB}$ = 20.4 Hz, $J_{BX}$ = 8.6 Hz, OCC$\underline{H}_2$CH), 2.06 (br m, 2, C$\underline{H}_2$CH=CH$_2$), and 1.45 ppm (br m, 5, C$\underline{H}$(C$\underline{H}_2$)$_2$C$\underline{H}_2$). Anal. Calcd. for $C_{13}H_{17}O_3Br$: C, 49.2; H, 5.4; Br, 25.2. Found: C, 48.9; H, 5.7; Br, 25.2.

In Example 6, the temperature at which the reaction of bromine with Compound V is allowed to occur is kept at 0°C in order to minimize the reaction of bromine with the double bond in the side chain of the compound. Temperatures up to 25°C could be used for this reaction but 0°C is preferred. A lower temperature limit of about −10°C is set since the rate of the desired reaction becomes too low at temperatures much below −10°C and because the reaction mixture freezes.

EXAMPLE 7

This example illustrates the preparation of methyl 6-(4-pentenyl)-β-resorcylate VII by the following general reaction wherein W = 3 and R = methyl:

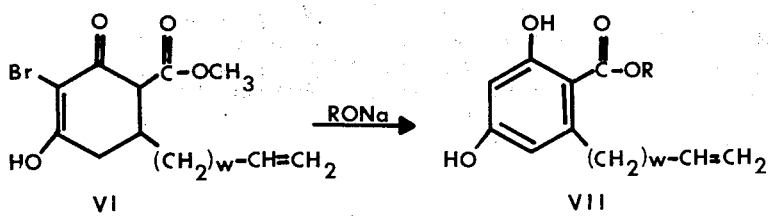

R = methyl or ethyl

A solution of 21.5 g, 0.0678 mol, of VI and sodium methoxide (prepared from 15.6 g, 0.678 g-atom of sodium) in 350 ml of anhydrous methanol was maintained at reflux under nitrogen for 9 hr. Then 200 ml of methanol was evaporated under vacuum. The reaction mixture was held at 0° while enough water to give 400 ml of the mixture was added to it. It was acidified with sulfuric acid (6 N), and extracted with ether (3 × 200 ml). The extract was washed with water (4 × 200 ml). Then it was decolorized with charcoal, and evaporated (Rinco) to yield 14.9 g, 0.0632 mol (93 percent), of crude VII. Purification by dry column chromatography (300 g, Silica Gel H, 10 percent ethyl ether in methylene chloride) yielded fractions that gave product that was recrystallized from ligroin (60–68°) to give 8.82 g, 0.0373 mol (55 percent), of pure VII: mp 55–56°; nmr (CDCl$_3$, TMS) δ11.83 (s, 1, hydrogen bonded 2-O$\underline{H}$), 6.90 (s, 1, 4-OH), 6.33 and 6.30 (2 d, 2, J = 2 Hz, aromatic C$\underline{H}$), 5.72, 4.92 and 4.88 (3 m, 3, C$\underline{H}$=C$\underline{H}_2$), 3.82 (s, 3, C$\underline{H}_3$), 2.82 (t, 2, J = 7 Hz, ArC$\underline{H}_2$), 2.08 (br m, 2, C$\underline{H}_2$CH=CH$_2$), and 1.64 ppm (br m, 2, CH$_2$C$\underline{H}_2$CH$_2$). Anal. Calcd. for $C_{13}H_{16}O_4$: C, 66.2; H, 6.8. Found: C, 66.1; H, 6.7.

In Example 7, the de-hydrobromination of compound VI can be effected at temperatures in the range 60°C–120°C but a temperature near 65°C is preferred.

The de-hydrobromination step could be carried out in a menstruum of an alcohol other than methanol, for example ethanol or butanol.

EXAMPLE 8

This example illustrates the preparation of ethyl 6-(4-pentenyl)-β-resorcylate VIII by the following general reaction wherein W = 3 and R = ethyl:

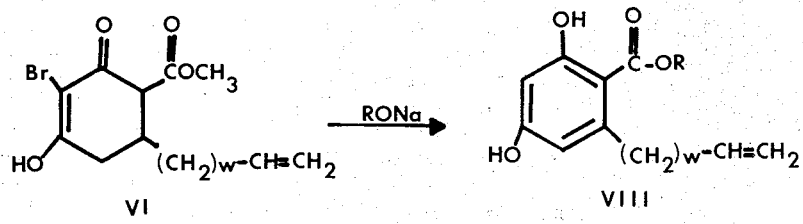

A solution containing 19.33 g, 0.0610 mol, of VI, and sodium ethoxide (prepared from 9.00 g, 0.391 g-atom, of sodium and in the 250 ml of ethanol) was held at reflux under nitrogen for 6 hr, and then it was evaporated under vacuum until its volume was about 100 ml. It was diluted with water to 300 ml, and acidified with sulfuric acid (6N) while it was held at 0°. The resulting mixture was extracted with ether (3 × 150 ml). The extract was then washed with water (4 × 100 ml), decolorized with charcoal, and evaporated (Rinco) to yield 14.0 g, 0.0562 mol (92 percent), of crude VIII. Dry column chromatography (300 g Silica Gel H, 10 percent ethyl ether in methylene chloride gave 9.15 g, 0.0366 mol (60 percent), of VIII: nmr (CDCl$_3$, TMS) δ11.95 (s, 1, 2-O$\underline{H}$), 7.42 (s, 1, 4-O$\underline{H}$), 6.33 and 6.30 (2 d, 2, J = 2 Hz, aromatic C$\underline{H}$), 5.72, 4.92 and 4.88 (3 m, 3, C$\underline{H}$=C$\underline{H}_2$), 4.40 (q, 2, J = 7 Hz, COOC$\underline{H}_2$), 2.85 (t, 2, J = 7 Hz, ArC$\underline{H}_2$), 2.03 (m, 2, C$\underline{H}_2$CH=CH$_2$), 1.64 (br m, 2, C$\underline{H}_2$CH$_2$CH$_2$), and 1.40 ppm (t, 3, J = 7 Hz, C$\underline{H}_3$). Except for the expected differences, this nmr spectrum is the same as that of VII.

EXAMPLE 9

This example illustrates the preparation of ethyl 6-(4-pentenyl)-β-resorcylate dibenzyl ether IX by the following general reaction wherein W = 3 and R = ethyl:

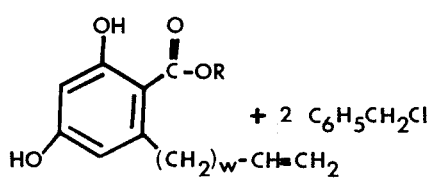
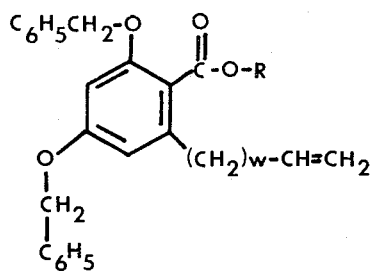

VIII

IX

+ 2 $C_6H_5CH_2Cl$

R = methyl or ethyl

A mixture of 31.5 g, 0.126 mol, VIII, 60.5 g of anhydrous potassium carbonate, and 31.5 ml 0.274 mol, of benzyl chloride in 300 ml of dimethylsulfoxide was stirred on a steam bath for 6 hr. 1.0 l of water was added to it while it was stirred, and then it was held overnight at −15°. The product that had crystallized was collected on a filter, and it was recrystallized from a mixture of ethyl ether and ligroin (bp 60°–68°) to give 45.5 g, 0.106 mol (84 percent), of IX: mp 49°–51°; nmr (CDCl$_3$, TMS) δ7.32 (m, 10, C$_6$H$_5$), 6.44 (s, 2, aromatic CH,) 5.72, 4.92 and 4.88 (3 m, 3, CH=CH$_2$), 4.98 and 4.96 (2 s, 4, C$_6$H$_5$CH$_2$), 4.28 (q, 2, J = 7 Hz, COOCH$_2$), 2.58 (t, 2, J = 7 Hz, ArCH$_2$), 2.00 (m, 2, CH$_2$CH=CH$_2$), 1.64 (br m, 2, CH$_2$CH$_2$CH$_2$), and 1.23 ppm (t, 3, J = 7 Hz, CH$_3$). Anal. Calcd. for C$_{28}$H$_{30}$O$_4$: C, 78.2; H, 7.0. Found: C, 78.0; H, 6.9

EXAMPLE 10

This example illustrates the preparation of 4-penten-2-yl 6-(4-pentenyl)-β-resorcylate dibenzyl ether X by the following general reaction wherein W = 3, R = ethyl and Z = 1.

0.97 g 0.042 mol, of sodium was added to a solution of 10.0 ml of 4-penten-2-ol (dried by distillation from its sodium alkoxide) in 75 ml of toluene (dried by distillation from sodium). The reaction mixture was stirred at 100° under nitrogen until the sodium had been consumed. Then 6.00 g, 0.0140 mol of IX (thoroughly dried under high vacuum at 55° in 10 ml of toluene was added to it, and it was stirred at 100° under nitrogen for 36 hr. The bronw reaction mixture was held at 0° while it was acidified with dilute hydrochloric acid. The organic layer was separated, and was washed with water (3 × 50 ml), decolorized with charcoal, and dried MgSO$_4$). Evaporation (Rinco) gave a residue that was purified by dry column chromatography (150 g of Silica Gel H, 10 percent ethyl ether in methylene chloride) to give 4.68 g, 0.00995 mol (71 percent), of X. Sublimation of this product gave pure X: nmr (CDCl$_3$, TMS) δ7.32 (m, 10, C$_6$H$_5$), 6.46 and 6.43 (2 s, 2, aromatic CH), 5.72, 4.92 and 4.88 (3 m, 6, CH=CH$_2$), 5.25 (br m, 1, COOCH), 5.01 and 4.99 (2 s, 4, C$_6$H$_5$CH$_2$), 2.60 (t, 2, J = 7 Hz, ArCH$_2$), 2.00 (br m, 4, CH$_2$CH=CH$_2$), 1.70 (br m, 2, CH$_2$CH$_2$CH$_2$), and 1.22 ppm (d, 3, J = 6.5 Hz, CH$_3$). Anal Calcd. for C$_{31}$H$_{34}$O$_4$: C, 79.2; H, 7.3. Found: C, 79.4; H, 7.2.

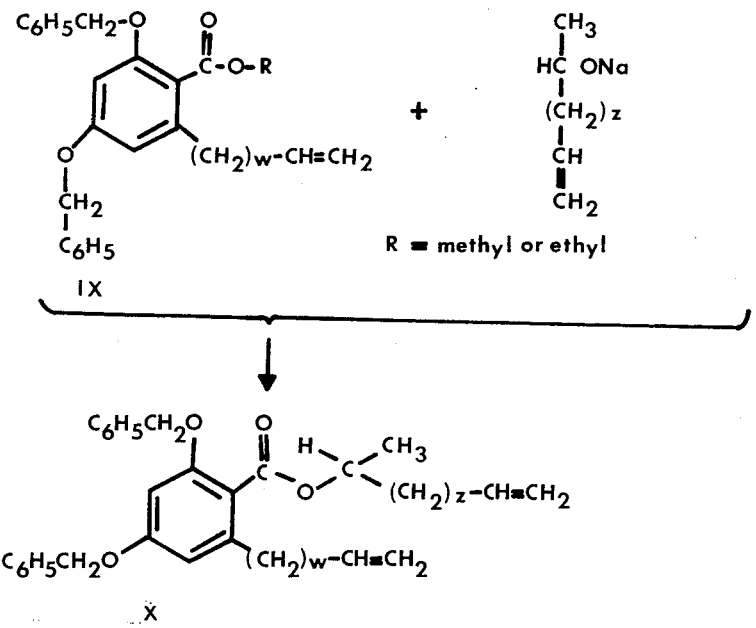

EXAMPLE 11

This example illustrates the preparation of zearalanone dibenzyl ether XI by the following general reaction wherein W = 3, X = 3, Y = 5 and Z = 1.

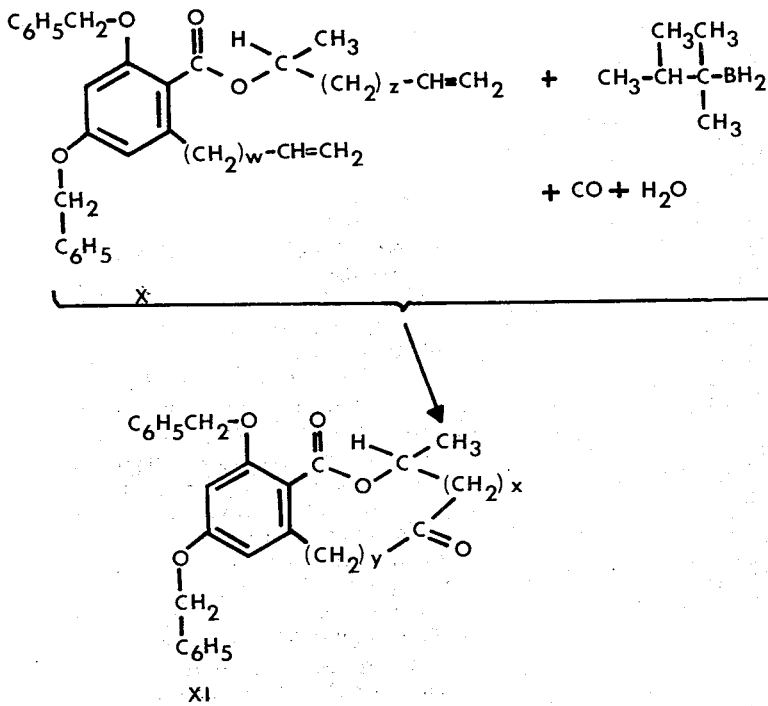

A solution of X in 60 ml of ether was freed of peroxides by vigorously shaking it for 5 min with 60 ml of a solution prepared from 60 g of $FeSO_4 \cdot 7H_2O$ and 6.0 ml of concentrated sulfuric acid in 110 ml of water. The ether solution was then washed with water (1 × 30 ml), 5 percent sodium hydroxide (1 × 30 ml), and water (5 × 30 ml). It was dried ($MgSO_4$), evaporated (Rinco), and held under high vacuum at 50° for 24 hrs. Then, a solution of 1.39 g, 2.95 × $10^{-3}$ mol, of this X in 80 ml of tetrahydrofuran (distilled from calcium hydride) was injected into a 100 ml, one neck round bottom flask equipped with efficient magnetic stirring, a rubber septum cap, and a nitrogen seal connected via a large-bore hypodermic needle in the septum. 6.96 ml, 0.00295 mol, of 0.424 M 2,3-dimethyl-2-butylborane in tetrahydrofuran was then injected dropwise into the reaction mixture that was stirred at 0°, according to the following schedule: 0 hr, 2.40 ml, over 10 min; 0.5 hr, 4.30 ml, over 10 min; 53.5. hr, 0.26 ml, over 2 min. The temperature was maintained at 25°C except during these additions. After 140 hr of stirring at 25°, 0.106 ml, 5.90 × $10^{-3}$ mol, of water was injected, a large-bore hypodermic needle was placed through the septum cap, and the flask was then sealed in a high pressure atuoclave that had been thoroughly flushed with carbon monoxide. The autoclave was maintained at 88 atm of carbon monoxide (C.P.) pressure, and at 60° for 11 hr while it was continually rocked. Then it was slowly vented, and the reaction mixture was again placed under a nitrogen seal. It was held at 25°with rapid stirring while 1.19 ml, 0.00357 mol, of 3.0 M sodium acetate, and 1.19 ml of 30 percent hydrogen peroxide were injected in rapid succession. The reaction mixture was then stirred at 50° for 7 hr. It was evaporated (Rinco), and the organic residue was dissolved in ether. This solution was washed with saturated potassium carbonate (1 × 15 ml), and water (3 × 15 ml), dried ($Na_2SO_4$), and evaporated (Rinco) to give 1.37 g of viscous residue that was separated by dry column chromatography (40 g of Silica Gel H containing 15 percent water; 10 percent ethyl acetate in benzene) to yield ca. 0.19 g, 0.00038 mol (13 percent), of pure XI: mp 103–105°; nmr ($CDCl_3$, TMS) $\delta 7.35$ (m, 10, $C_6\underline{H}_5$), 6.43 (s, 2, aromatic $C\underline{H}$), 5.24 (br m, 1, $COOC\underline{H}$), 5.01 and 4.98 (2 s, 4, benzyl $C\underline{H}_2$), 2.58 (br m, 2, $ArC\underline{H}_2$), 2.37 (t, 4, J = 6.0 Hz, $C\underline{H}_2COC\underline{H}_2$), 1.50 (br m, 10, $(C\underline{H}_2)_2CH_2COCH_2(C\underline{H}_2)$), and 1.13 ppm (d, 3, J = 6.5 Hz, $C\underline{H}_3$); mass spectrum (70 eV) m/e (rel intensity) 500(6), 482(2),409(2), 391(2), 181(6), 91(100), 69(2), 65(4), 32(2), 28(8). The nmr and mass spectra are identical to those of the dibenzyl ether of zearalanone perpared from natural zearalenone. The melting point is the same as that of XI prepared via other sequences, and mixed melting points are not depressed.

In Example 11, the reaction between Compound X and 2,3-dimethyl-2-butylborane was carried out at 25°C. however, the reaction may be conducted in the range of 15°C–50°C. This temperature can be raised to 50°C but yields fall off beyond this value. Temperatures much lower than 25°C are not practical since the rate of reaction is too low at the lower temperatures.

The reaction with carbon monoxide may be at a temperature in the range of 25°–80°C and can be carried out at temperatures above 60°C, but the yields will be lower if this value is exceeded by say 20°C. Lower tmperatures, e.g. down to room temperature, can be used if longer reaction times can be tolerated. An increase in carbon monoxide pressure will, of course, increase the reaction rate and make lower temperatures more acceptable.

EXAMPLE 12

This example illustrates the preparation of DL-zearalanone XII by the following general reaction wherein X = 3 and Y = 5:

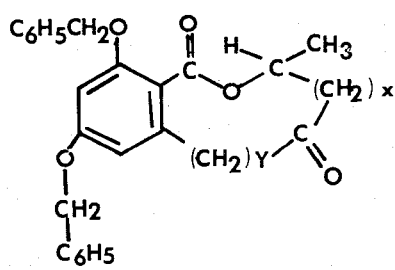

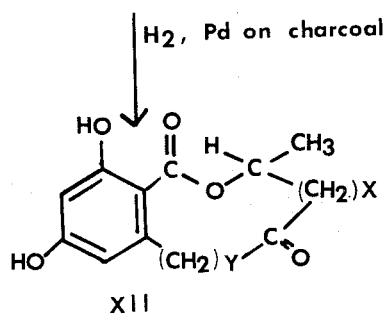

DL-Zearalanone when X = 3 and Y = 5 (R,S)-zearalanone

A solution of 0.100 g, 0.0002 mol, of XI in 10.0 ml of ethyl acetate and 4.0 ml of absolute ethanol with 0.05 g of 10 percent palladium on charcoal catalyst and three drops of triethylamine added was hydrogenated at 1 atm until hydrogen consumption ceased. The reaction mixture was then filtered and evaporated (Rinco), and the residue was purified by preparative thin layer chromatography (Silica Gel, 10 percent ethyl acetate in benzene) to give 0.054 g, 0.000169 mol (84 percent), of XII: mp 208–210° (from acetone); nmr (acetone-$d_6$, TMS) $\delta$11.87 (br s, 1, 2-O$\underline{H}$), 6.32 (d, 1, J = 2.5 Hz, aromatic C$\underline{H}$), 6.28 (d, 1, J = 2.5 Hz, aromatic C$\underline{H}$), 7.34 (br s, 1, 4-O$\underline{H}$), 5.20 (br m, 1, COOC$\underline{H}$), 3.02 and 2.74 (2 br m, 6, ArC$\underline{H}_2$ and C$\underline{H}_2$COC$\underline{H}_2$ ), 2.50 to 1.20 (very br m, 10, CH$_2$(C$\underline{H}_2$)$_3$CH$_2$ and CH(C$\underline{H}_2$)$_2$CH$_2$), and 1.32 ppm (d, 3, J = 6.0 Hz, C$\underline{H}_3$); mass spectrum (70 eV) m/e (rel intensity) 320(35), 302(19), 251(19), 177(36), 163(98), 150(35), 69(46), 55(76), 41(100). These nmr and mass spectra are identical to those of naturally-derived S-zearalanone.

In Example 12, a palladium-on-charcoal catalyst is used for replacing the benzyl groups with hydrogen atoms. Other mild hydrogenation catalysts such as platinum-on-charcoal can be used for this purpose.

We claim:
1. A method for the preparation of (R,S)-zearalanone dibenzyl ether comprising reacting 4-penten-2-yl 6-(4-pentenyl)-β-resorcylate with 2,3-dimethyl-2-butylborane to give a tertiary alkyl borane that is then reacted with carbon monoxide under super-atmospheric pressure and then with hydrogen peroxide.

2. A method for the preparation of (R,S)-zearalanone dibenzyl ether comprising reaction 4-penten-2-yl 6-(4-pentenyl)-β-resorcylate with 2,3-dimethyl-2-butylborane at a temperature in the range 15°C–50°C to give a tertiary alkyl borane that is then reacted with carbon monoxide under super-atmospheric pressure at a temperature in the range 25°C–80°C and then with hydrogen peroxide.

3. A method for the chemical synthesis of (R,S)-zearalanone wich comprises the steps of
  a. reacting 5-hexenal with malonic acid to prepare 2,7-octadienoic acid;
  b. reacting 2,7-octadienoic acid with diazomethane to prepare methyl 2,7-octadienoate;
  c. reacting methyl 2,7-octadienoate with the sodium salt of acetoacetic ester in the presence of methanol and sodium methoxide to prepare the sodium salt of methyl 6-(4-pentenyl)-β-dihydro-resorcylate;
  d. reacting the sodium salt of methyl 6-(4-pentenyl)-β-dihydroresorcylate with bromine to prepare methyl 3-bromo-6-(4pentenyl)-β-dihydroresorcylate; -pentenyl)-β
  e. reacting methyl 3-bromo-6-(4-pentenyl)-β-dihydro-resorcylate with sodium ethoxide to prepare ethyl 6-(4-pentenyl)-β-resorcylate;
  f. reacting ethyl 6-(4-pentenyl)-β-resorcylate with benzyl chloride to prepare ethyl 6-(4-pentenyl)-β-resorcylate dibenzyl ether;
  g. reacting ethyl 6-(4-pentenyl)-β-resorcylate dibenzyl ether with the sodium alcoholate of 4penten-2ol to prepare 4-penten-2-yl 6-(pentenyl)β-resorcylate dibenzyl ether;
  h. reacting 4-penten-2yl 6-(4-pentenyl)-β-resorcylate with 2,3-dimethyl-2-butyl borane to give a tertiary alkyl borane that is then reacted with carbon monoxide under super-atmospheric pressure and then with hydrogen peroxide to prepare (R,S)-zearalanone dibenzyl ether;
  i. reacting (R,S)-zearalanone dibenzyl ether with hydrogen to prepare (R,S)-zearalanone.

* * * * *

UNITED STATES PATENT AND TRADEMARK OFFICE
CERTIFICATE OF CORRECTION

PATENT NO. : 3,957,825
DATED : May 18, 1976
INVENTOR(S) : WILBERT H. URRY and GUY TOWNS MULLENBACH It is certified that error appears in the above-identified patent and that said Letters Patent are hereby corrected as shown below:

Column 2, between formulae III and V, "$CH_3-ON_3$" should read --$CH_3-ONa$--

Column 2, formula VIII should appear

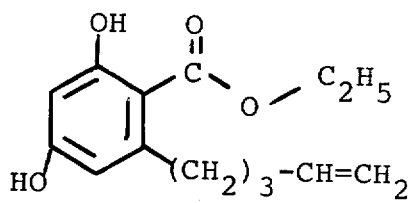

VIII

Column 2, under the last formula, after "XII" should appear --(R,S)-zearalanone--

Column 3, line 41, "3" should be underscored

Column 3, line 42, "5" should be underscored

Column 4, line 35, "$\pi$" should appear -- $\tau$ --

UNITED STATES PATENT AND TRADEMARK OFFICE
CERTIFICATE OF CORRECTION

PATENT NO. : 3,957,825
DATED : May 18, 1976
INVENTOR(S) : WILBERT H. URRY and GUY TOWNS MULLENBACH It is certified that error appears in the above–identified patent and that said Letters Patent are hereby corrected as shown below:

Column 5, the formula spanning lines 42 to 51 should read:

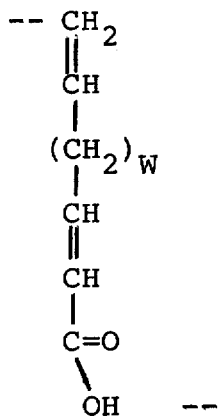

Column 7, line 16, the first formula in the line should read --$\underline{CH}_2$CH=CH$_2$)--

Column 8, line 69, "3.25" should read --3.35--

Column 14, line 41, the formula within the parentheses should read --($\underline{CH}_2$)$_2$CH$_2$COCH$_2$($\underline{CH}_2$)3),--

Claim 3, line 30 of the column, a hyphen should appear after "4"

Claim 3, line 31 of the column, "pentenyl)-β" should be deleted

Claim 3, line 40 of the column, hyphens should appear after "4" and "2"

UNITED STATES PATENT AND TRADEMARK OFFICE
CERTIFICATE OF CORRECTION

PATENT NO. : 3,957,825
DATED : May 18, 1976
INVENTOR(S) : WILBERT H. URRY and GUY TOWNS MULLENBACH It is certified that error appears in the above-identified patent and that said Letters Patent are hereby corrected as shown below:

Claim 3, line 41 of the column, before "pentenyl" should appear --4- -- and a hyphen should appear before "β"

Claim 3, line 43 of the column, a hyphen should appear after "2".

Signed and Sealed this

Seventh Day of September 1976

[SEAL]

Attest:

RUTH C. MASON
*Attesting Officer*

C. MARSHALL DANN
*Commissioner of Patents and Trademarks*